(12) United States Patent
Shelton, IV et al.

(10) Patent No.: US 10,709,440 B2
(45) Date of Patent: Jul. 14, 2020

(54) SUTURE PASSING INSTRUMENT WITH PUNCTURE SITE IDENTIFICATION FEATURE

(71) Applicant: ETHICON LLC, Guaynabo, PR (US)

(72) Inventors: Frederick E. Shelton, IV, Hillsboro, OH (US); Jason L. Harris, Lebanon, OH (US); Rebecca J. Gettinger, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 255 days.

(21) Appl. No.: 15/637,712

(22) Filed: Jun. 29, 2017

(65) Prior Publication Data

US 2019/0000444 A1 Jan. 3, 2019

(51) Int. Cl.
| | |
|---|---|
| *A61B 17/04* | (2006.01) |
| *A61B 17/00* | (2006.01) |
| *A61B 17/06* | (2006.01) |
| *A61B 90/00* | (2016.01) |

(52) U.S. Cl.
CPC ...... *A61B 17/0485* (2013.01); *A61B 17/0057* (2013.01); *A61B 17/0469* (2013.01); *A61B 17/0483* (2013.01); *A61B 17/06066* (2013.01); *A61B 17/06109* (2013.01); *A61B 2017/00623* (2013.01); *A61B 2017/00637* (2013.01); *A61B 2017/00663* (2013.01); *A61B 2017/00672* (2013.01); *A61B 2017/06042* (2013.01); *A61B 2017/06095* (2013.01); *A61B 2090/033* (2016.02)

(58) Field of Classification Search
CPC ............ A61B 17/0057; A61B 17/0469; A61B 17/0482; A61B 17/0483; A61B 17/0485; A61B 17/06109; A61B 17/3417; A61B 17/3421; A61B 17/0401; A61B 2017/06042; A61B 17/00234; A61B 2017/06009; A61B 2017/06019; A61B 2090/033; A61M 5/3291

See application file for complete search history.

(56) References Cited

U.S. PATENT DOCUMENTS

| | | | |
|---|---|---|---|
| 5,618,290 A | 4/1997 | Toy et al. | |
| 5,792,135 A | 8/1998 | Madhani et al. | |
| 5,817,084 A | 10/1998 | Jensen | |
| 5,878,193 A | 3/1999 | Wang et al. | |

(Continued)

FOREIGN PATENT DOCUMENTS

WO WO 2006/023975 A2 3/2006

OTHER PUBLICATIONS

Free Dictionary Definition of "Fixedly", accessed on Oct. 28, 2019, <https://www.thefreedictionary.com/fixedly>.*

(Continued)

*Primary Examiner* — Elizabeth Houston
*Assistant Examiner* — Mohamed G Gabr
(74) *Attorney, Agent, or Firm* — Frost Brown Todd LLC

(57) ABSTRACT

A surgical instrument and method for indicating a tissue penetration site includes an inner needle and a head. The inner needle has a driver configured to translate the inner needle form a first position to a second position. The head is securely attached to the inner needle at an end opposite the driver and is configured to expand from a contracted state to an expanded state and thereby indicate the tissue penetration site.

20 Claims, 11 Drawing Sheets

(56) References Cited

U.S. PATENT DOCUMENTS

| | | |
|---|---|---|
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,524,320 B2 | 4/2009 | Tierney |
| 7,691,098 B2 | 4/2010 | Wallace et al. |
| 7,806,891 B2 | 10/2010 | Nowlin et al. |
| 7,981,092 B2 | 7/2011 | Duke |
| 8,226,553 B2 | 7/2012 | Shelton, IV et al. |
| 8,251,900 B2 | 8/2012 | Ortiz et al. |
| 8,479,969 B2 | 7/2013 | Shelton, IV |
| 8,568,362 B2 | 10/2013 | Moreno et al. |
| 8,573,461 B2 | 11/2013 | Shelton, IV et al. |
| 8,573,465 B2 | 11/2013 | Shelton, IV |
| 8,579,807 B2 | 11/2013 | Moreno et al. |
| 8,602,288 B2 | 12/2013 | Shelton, IV et al. |
| 8,616,431 B2 | 12/2013 | Timm et al. |
| 8,636,686 B2 | 1/2014 | Minnelli et al. |
| 8,690,831 B2 | 4/2014 | Duke |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 9,301,759 B2 | 4/2016 | Spivey et al. |
| 9,351,721 B2 | 5/2016 | Auerbach et al. |
| 9,687,226 B2 | 6/2017 | Hodgkinson et al. |
| 9,700,303 B2 | 7/2017 | Prior et al. |
| 10,172,597 B2 * | 1/2019 | Geist .................. A61B 10/0275 |
| 2004/0249393 A1 * | 12/2004 | Weisel ............. A61B 17/06109 606/144 |
| 2006/0089609 A1 * | 4/2006 | Bleich ................ A61B 17/1659 604/272 |
| 2008/0200950 A1 | 8/2008 | Wohlert |
| 2009/0093809 A1 * | 4/2009 | Anderson .......... A61B 17/0057 606/41 |
| 2010/0063351 A1 * | 3/2010 | Witzmann ......... A61B 17/0401 600/31 |
| 2015/0038793 A1 * | 2/2015 | Prior .................... A61M 5/329 600/204 |
| 2015/0320417 A1 * | 11/2015 | Stewart .............. A61B 17/0469 606/144 |
| 2016/0120518 A1 * | 5/2016 | Geist .................. A61B 10/0275 600/566 |
| 2017/0281154 A1 | 10/2017 | Hess et al. |

OTHER PUBLICATIONS

U.S. Appl. No. 15/637,683, filed Jun. 29, 2017.
U.S. Appl. No. 15/637,688, filed Jun. 29, 2017.
U.S. Appl. No. 15/637,690, filed Jun. 29, 2017.
U.S. Appl. No. 15/637,696, filed Jun. 29, 2017.
U.S. Appl. No. 15/637,702, filed Jun. 29, 2017.
U.S. Appl. No. 15/637,707, filed Jun. 29, 2017.
U.S. Appl. No. 15/637,735, filed Jun. 29, 2017.
U.S. Appl. No. 15/637,778, filed Jun. 29, 2017.
European Search Report and Written Opinion dated Aug. 16, 2018 for Application No. EP 18180474.1, 8 pgs.
International Search Report and Written Opinion dated Sep. 12, 2018 for Application No. PCT/IB2018/054543, 11 pgs.
European Examination Report dated Oct. 14, 2019 for Application No. EP 18180474.1, 5 pgs.

* cited by examiner

SUTURE PASSING INSTRUMENT WITH PUNCTURE SITE IDENTIFICATION FEATURE

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparascopic and endoscopic surgical procedures, may access the cavity through a trocar assembly. Trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Merely exemplary trocar assemblies, components thereof, and other varieties of wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008; U.S. Pat. Pub. No. 2015/0038793, entitled "Devices, Systems, and Methods for Providing Surgical Access and Facilitating Closure of Surgical Access Openings," published on Feb. 5, 2015; U.S. Pat Pub. No. 2015/0038994, entitled "Devices, Systems, and Methods for Providing Surgical Access and Facilitating Closure of Surgical Access Openings," published on Feb. 5, 2015; and U.S. Pat. Pub. No. 2015/0094741, entitled "Wound Closure Device including Mesh Barrier." Published on Apr. 2, 2015. The disclosure of each of the above-cited U.S. Patents and Publications is incorporated by reference herein.

Surgical instruments for use with such trocars may have a distal end effector for engaging tissue through the trocar cannula in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including trocar assemblies and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
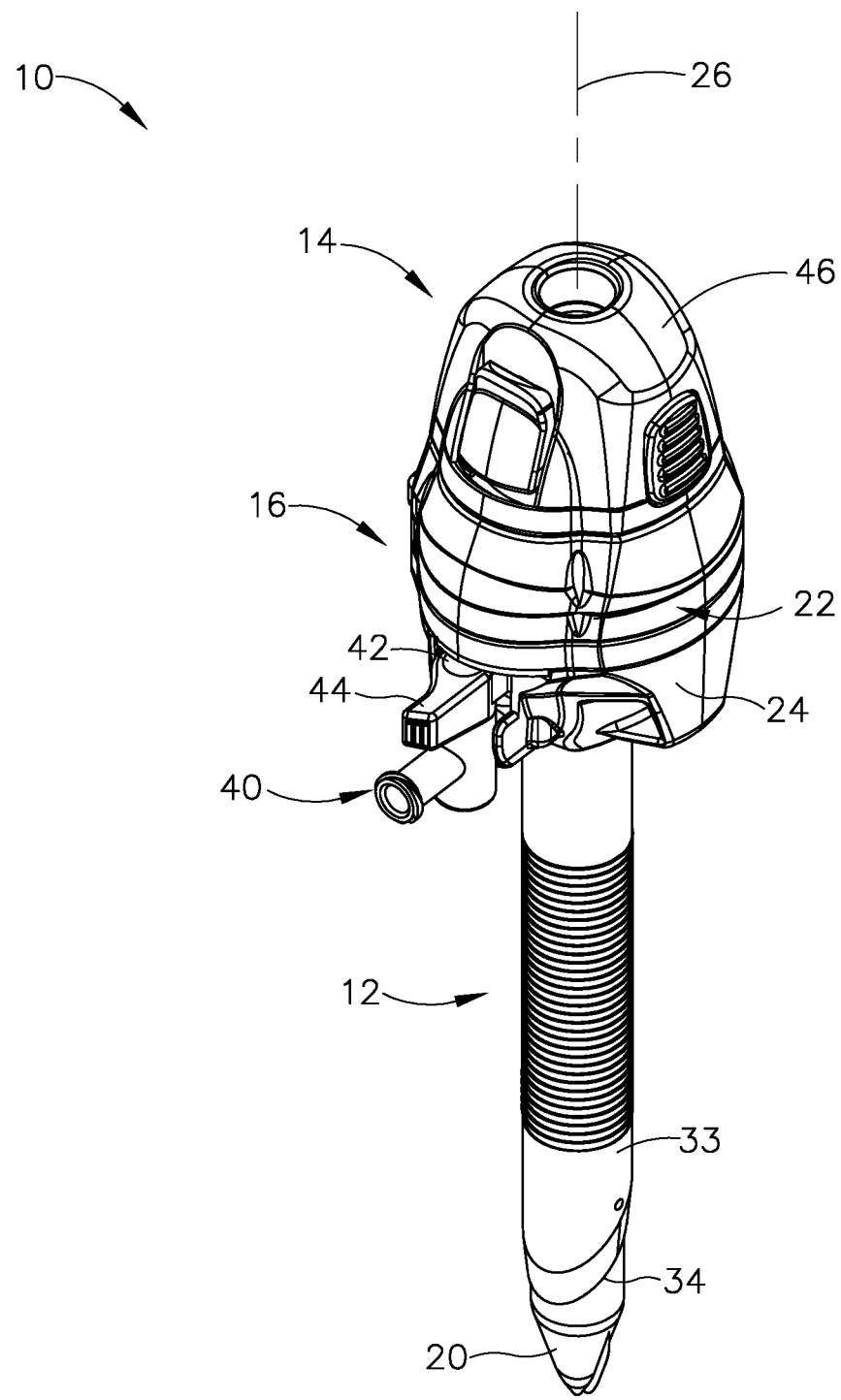
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 2:
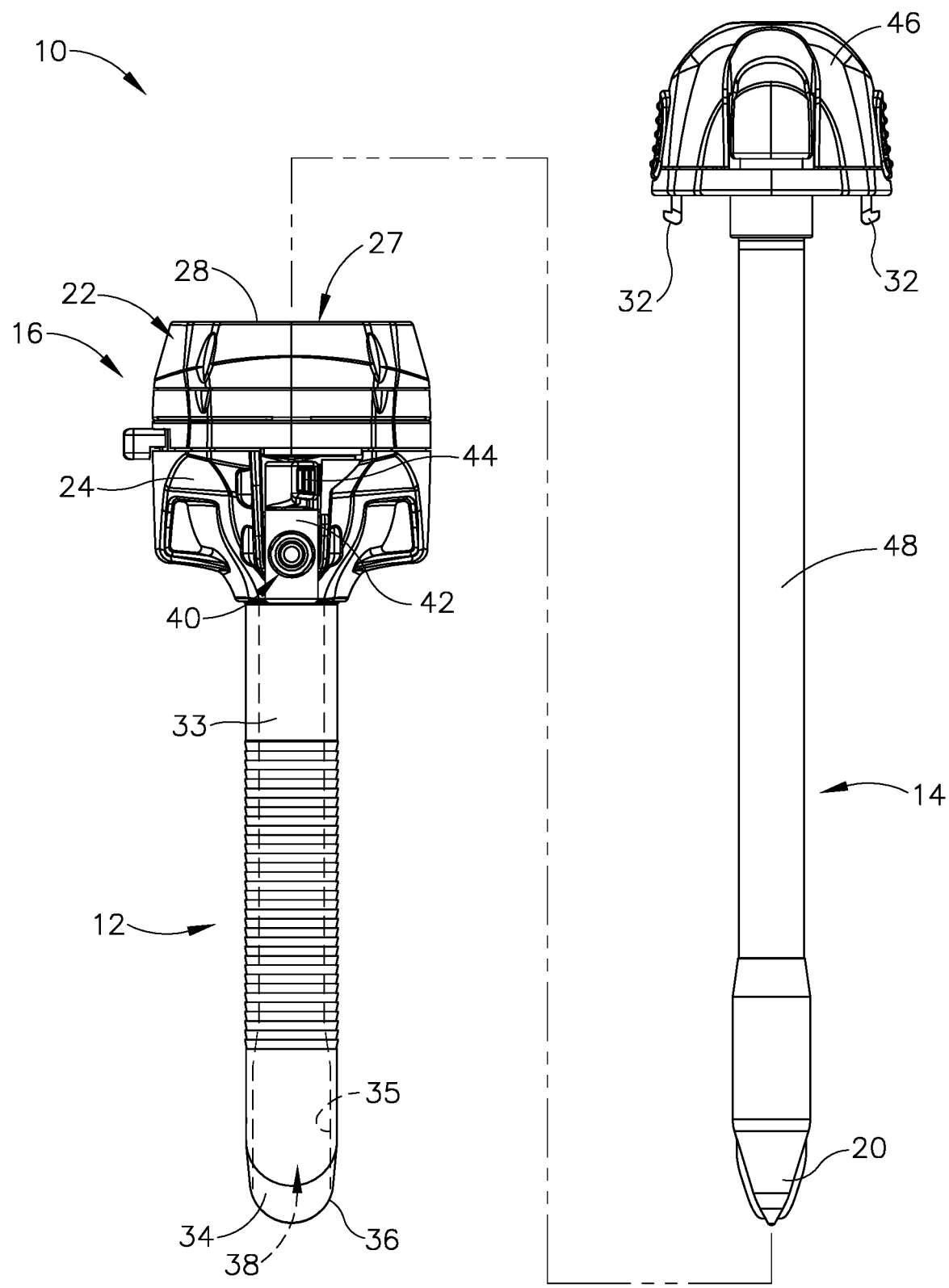
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly 10 through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening

(28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained with cap (22) and configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
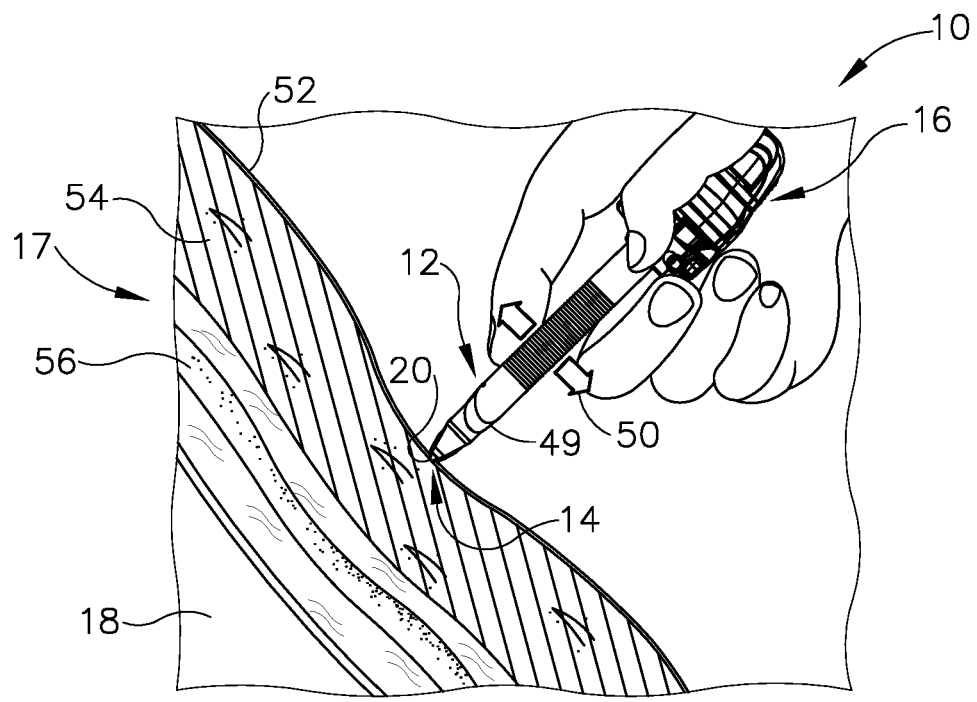
FIG. 3A depicts a sectional side view of tissue of a patient with the trocar assembly of FIG. 1 being manipulated by a clinician through the tissue.
Figure 3B:
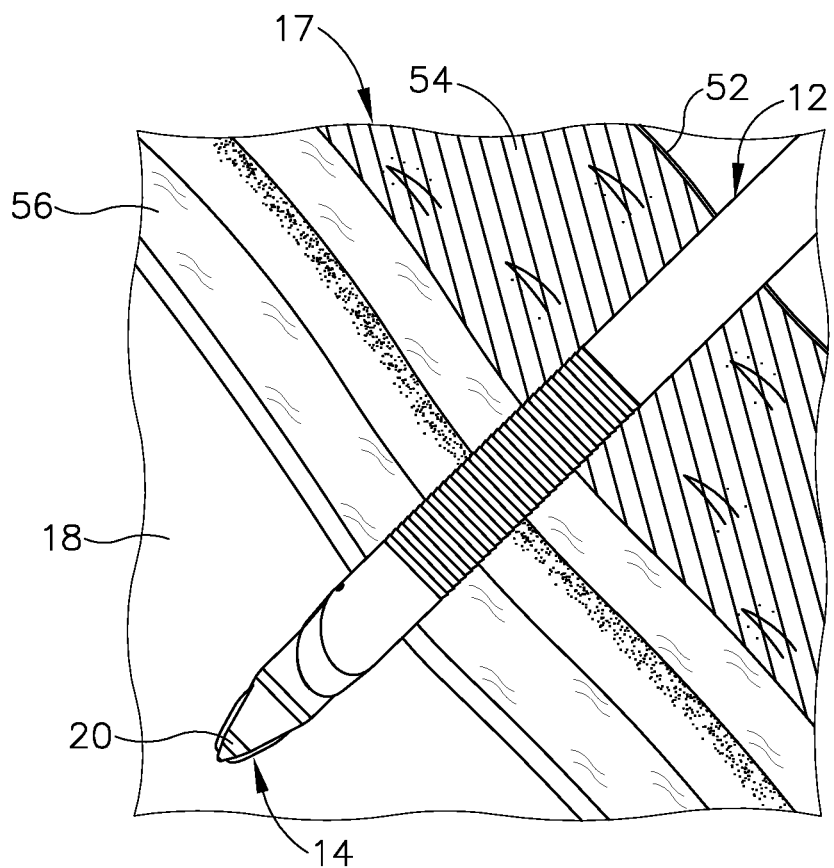
FIG. 3B depicts a sectional side view of the tissue and trocar assembly of FIG. 3A, with the trocar assembly of FIG. 1 inserted through the tissue and received within a cavity of the patient.
Figure 3C:
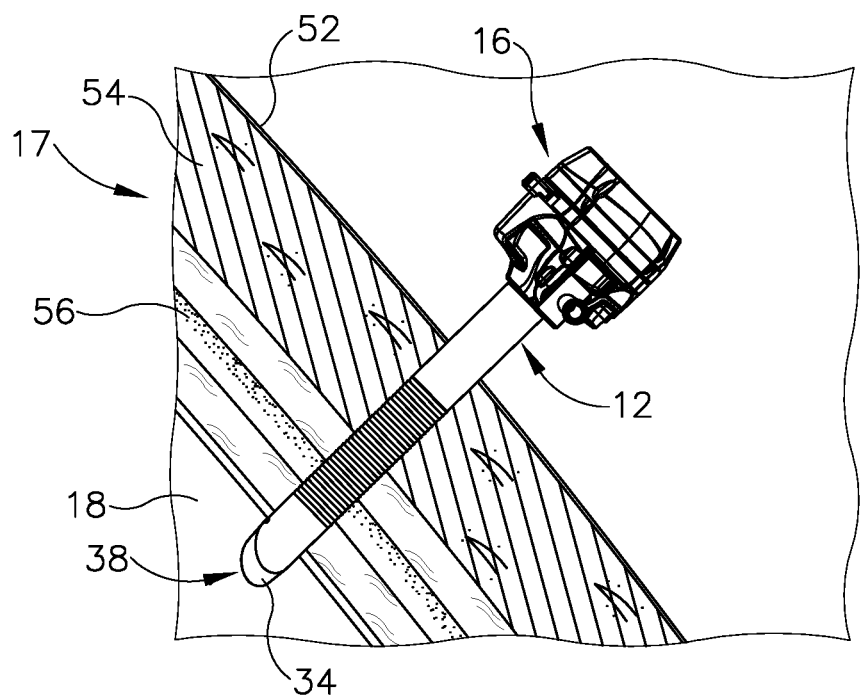
FIG. 3C depicts a sectional side view of the tissue and the trocar assembly of FIG. 3A, with the obturator withdrawn from the trocar cannula for accessing the cavity via a working channel through the trocar cannula and the trocar housing.
Figure 3D:
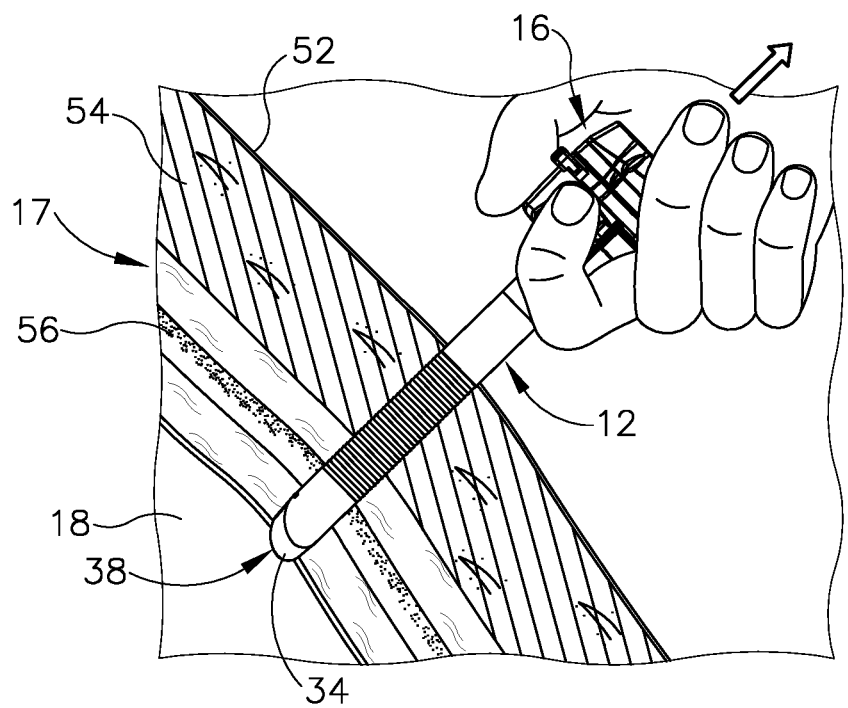
FIG. 3D depicts a sectional side view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
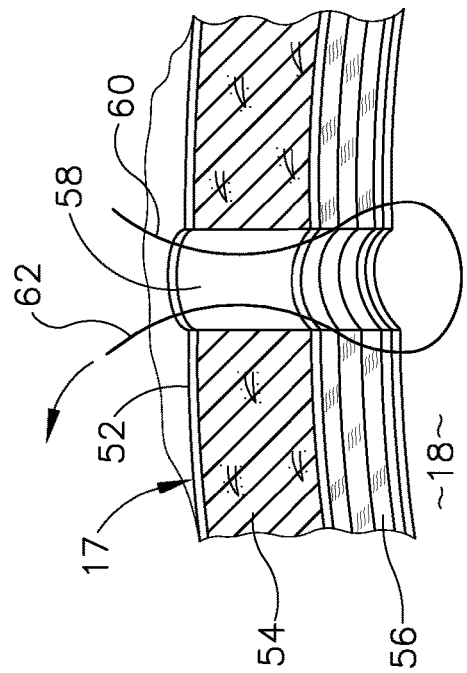
FIG. 4A depicts another sectional side view of the tissue shown in FIGS. 3A-3D following removal of the trocar assembly of FIG. 1, with an opening through the tissue and a suture thread being introduced into a portion of the tissue for suturing the opening closed.
Figure 4B:
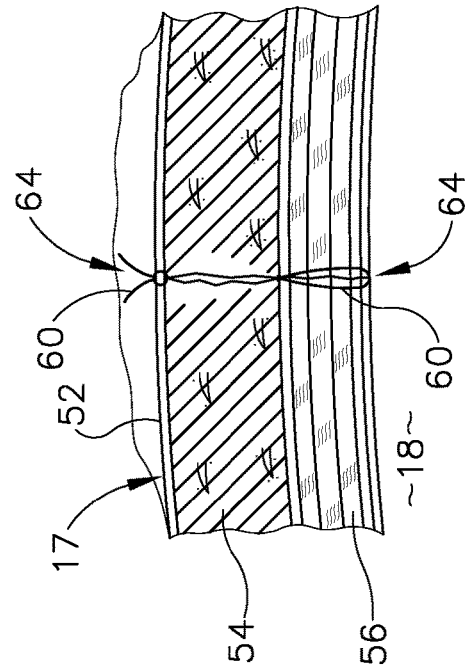
FIG. 4B depicts a sectional side view of the tissue of FIG. 4A, with the suture thread being introduced though another portion of the tissue and pulled through the tissue.
Figure 4C:
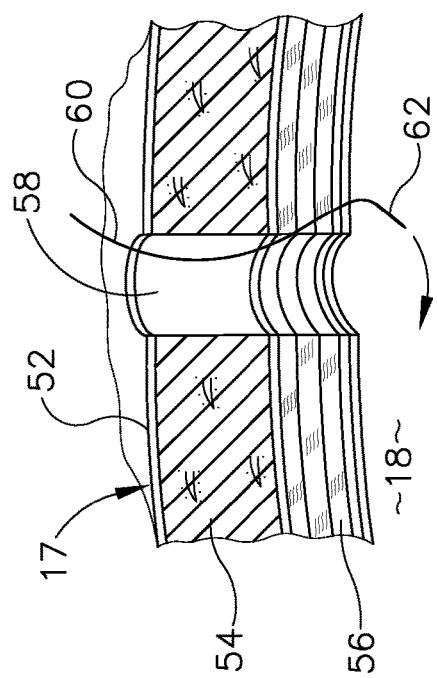
FIG. 4C depicts a sectional side view of the tissue of FIG. 4A, with the suture thread tightened and knotted for at least partially closing the opening.
Figure 4D:
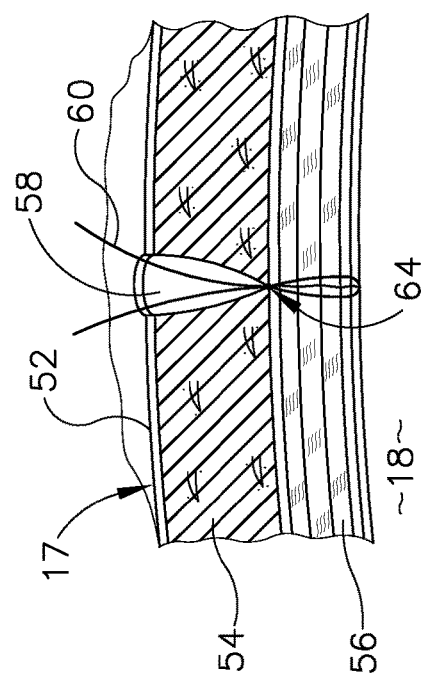
FIG. 4D depicts a sectional side view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread 60 through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance from tissue opening (58) in order to provide a relatively close proximity to tissue opening (58); but also at a sufficient distance to provide ample fascia (56) for anchoring suture thread (60) therein. As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed on Apr. 1, 2016, which is incorporated by reference herein in its entirety, describes an alternative trocar assembly and suturing technique. To this end, alternative trocar assemblies and suturing techniques may be used in any combination as desired by the clinician.

II. Exemplary Suture Passer with Puncture Site Identification Feature

Identifying the proper location to puncture through a patient's tissue to access an internal target site may be difficult in some instances, particularly when it is not readily apparent from the patient's outer skin layer where the internal target site is located. For example, the clinician may determine the location for puncturing a patient's tissue by utilizing their professional judgment with the expectation that the probability of accurately designating a desirable puncture site is measured. In instances where the determined location was not the desirable puncture site, the clinician may need to repair the patient's damaged tissue where the puncture had occurred and then subsequently identify an alternative site for puncturing through the patient's tissue. This occurrence may not only be detrimental to the patient's health and well-being but it may also be time consuming. It may thus be beneficial in such instances for a surgical instrument, such as any of suture passers (100, 200, 300) discussed below, to be capable of indicating where a potential puncture may occur within a patient's body based on the current positioning of the instrument while also inhibiting damage to the tissue during use.

The following description provides various exemplary suture passers (100, 200, 300) with respective needle heads (132, 232, 332) that are configured to designate a potential puncture site while inhibiting damage to the patient's tissue and subsequently puncturing the tissue upon confirmation of the desired location. Providing the capability to designate and puncture the tissue may thereby reduce the likelihood of the clinician misidentifying the location of the desirable puncture site. Suture passers (100, 200, 300) and needle heads (132, 232, 332) described below may be readily incorporated into any of the various surgical instruments described above and in any of the various surgical procedures described in the various references provided herein. Other suitable ways in which the below-described suture passers (100, 200, 300) and puncture site identification features may be used will be apparent to those of ordinary skill in the art in view of the teachings herein.

Figure 5:
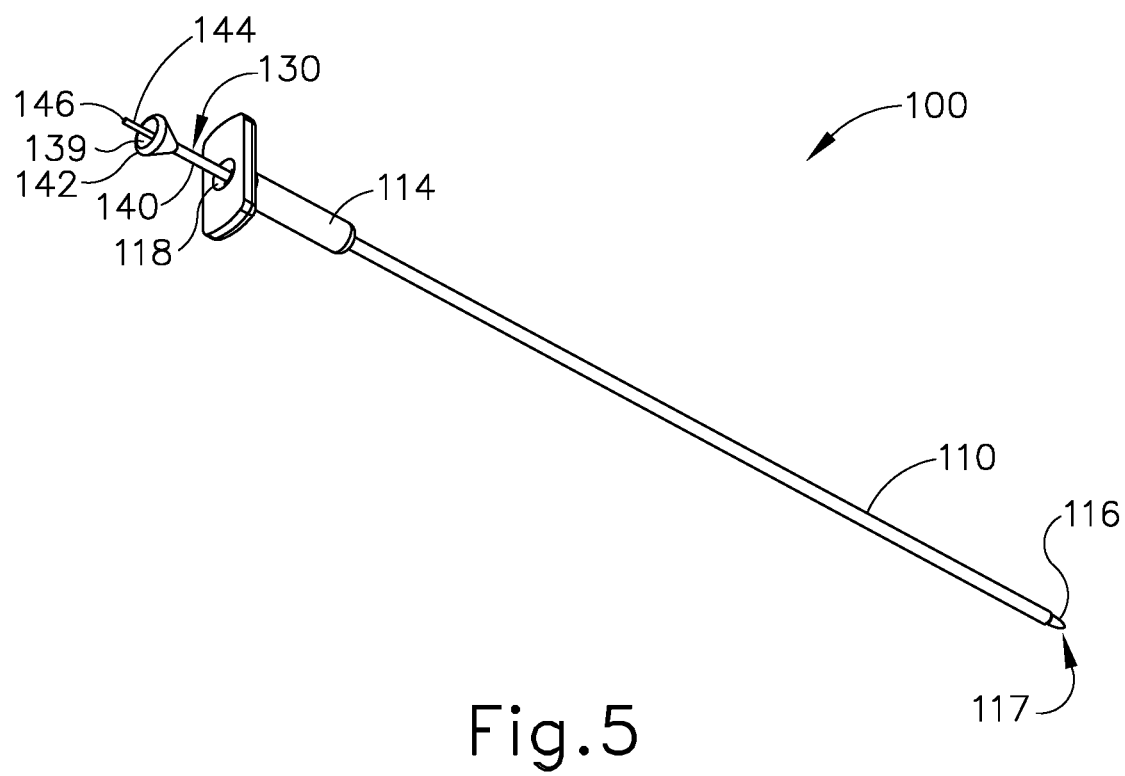
FIG. 5 depicts a perspective view of a first exemplary suture passer having an inner needle slidably received within an outer needle.

A. Exemplary Suture Passer with Deformable Head i. Exemplary Outer Needle with Pointed Tip FIGS. 5-6G show a first exemplary suture passer (100) comprising an outer sheath (110) and an inner needle (130). Inner needle (130) is substantially enclosed within outer sheath (110) such that the longitudinal length of inner needle (130) extends within an outer lumen (112) of outer sheath (110). Inner needle (130) comprises a needle head (132), a longitudinal shaft (140), and a driver (142). Longitudinal shaft (140) has a longitudinal length that separates needle head (132), which is positioned on a distal end of longitudinal shaft (140), from driver (142), which is positioned on an opposite, proximal end of longitudinal shaft (140). Driver (142) is in the form of a plunger that is configured to slidably translate inner needle (130) within outer lumen (112) of outer sheath (110). To this end, outer sheath (110), which may also be referred to herein as outer needle (110), comprises outer lumen (112), a housing (114), a distal tip (116) and a proximal opening (118). Distal tip (116) has a sharp point configured to puncture tissue (17) and includes a distal opening (117). Outer lumen (112) has a longitudinal length that separates opening (117) of distal tip (116) from housing (114) and proximal opening (118). Openings (117, 118) are in communication with outer lumen (112) and in axial alignment with the longitudinal length of outer lumen (112).

Inner needle (130) is inserted into outer sheath (110) by directing needle head (132) into proximal opening (118) and slidably advancing inner needle (130) through outer lumen (112) and toward distal opening (117). Inner needle (130) further comprises a cable (144) extending through an inner lumen (139) of inner needle (130). Cable (144) is securely attached on a distal end to needle head (132) and on a proximal end to an actuator (146). Actuator (146) extends out from inner lumen (139) through driver (142) and is operatively connected to needle head (132). Needle head (132) of inner needle (130) is formed of deflectable material, such as an elastomer, and may be flexible and/or elastic, and further configured to expand from a contracted state to an expanded state as shown respectively in FIG. 6A and FIG. 6D. In the present example, needle head (132) also is an atraumatic, blunt needle head (132) that is configured to not puncture tissue (17) and thus reduce the likelihood of damage to tissue (17) when extended beyond distal tip (116) in use. Of course, alternative examples of atraumatic ends may be so used, and the invention is not intended to be unnecessarily limited to blunt needle head (132) as shown.

Figure 6A:
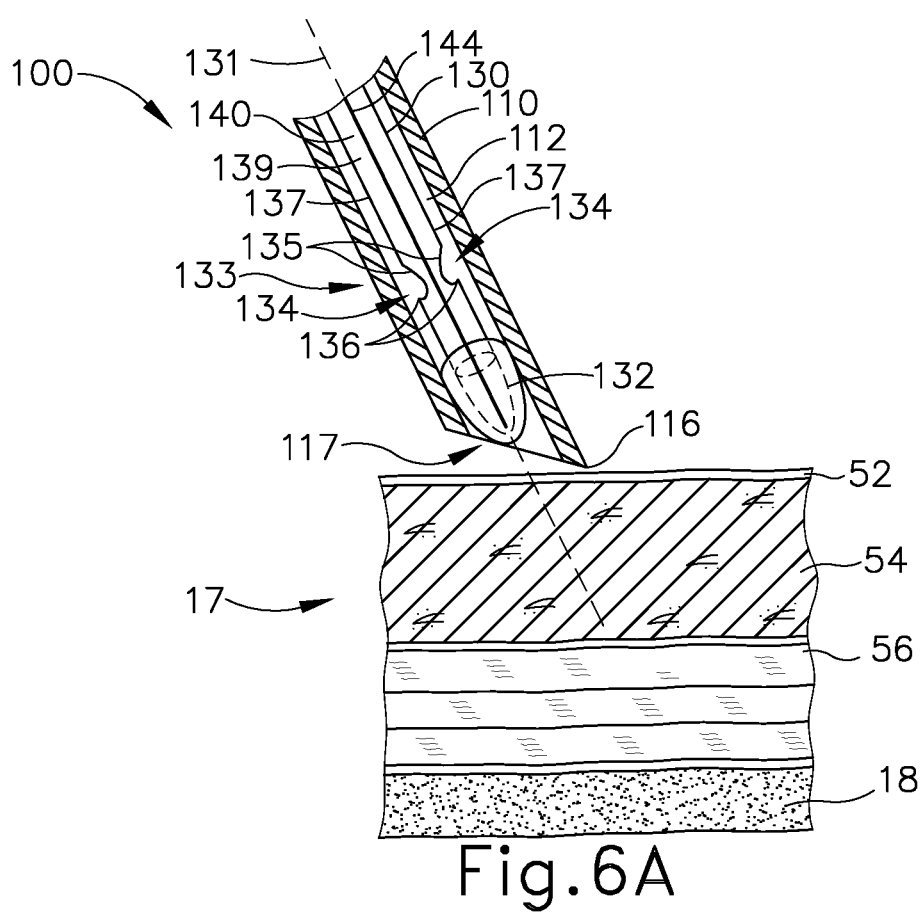
FIG. 6A depicts a partial cross-sectional view of the suture passer of FIG. 1, taken generally along a centerline thereof, with the suture passer positioned along a patient's outer layer of skin and the inner needle in a retracted position contained within the outer needle.

With respect to FIG. 6A, needle head (132) is configured to resiliently expand from the contracted state to the expanded state upon actuation of cable (144) by actuator (146). In the present example, proximal actuation of cable (144) pulls a distal portion of needle head (132) proximally toward a distal end of longitudinal shaft (140). A proximal portion of needle head (132) simultaneously abuts against the distal end of longitudinal shaft (140) thereby causing needle head (132) to umbrella radially outwardly to the expanded state (see FIG. 6D) relative to a longitudinal axis (131) of inner needle (130).

Inner needle (130) of the present example is resiliently biased toward a proximal, retracted position within outer lumen (112), such as by a coil spring or other kind of biasing member (not shown) operatively connected between inner needle (130) and outer sheath (110). To transition inner needle (130) from the retracted position (see FIG. 5) to a distal, extended position, the clinician exerts a distal force on driver (142) to thereby slidably advance inner needle (130) through outer lumen (112). The natural state of biasing member (not shown) generally positions suture passer (100) in the retracted position with needle head (132) confined within distal tip (116).

As a merely illustrative example, inner needle (130) is formed of a hardened stainless steel, such as a thick wall stainless steel tube stock, while the molded features on inner needle (130), particularly driver (142), are formed of plastic, such as polycarbonate. In another example, inner needle (130) may be form of a plastic material and metal coated for additional surface hardness similar to stainless steel with a bending strength similar to aluminum. Inner needle (130) has a diameter smaller than a diameter of outer sheath (110) such that inner needle (130) is slidably received within outer sheath (110). For example, inner needle (130) may have a diameter ranging from approximately 2 millimeters to approximately 3 millimeters and outer sheath (110) may have a corresponding larger diameter with ample clearance configured to receive a United States Pharmacopeia (U.S.P.) designation 2 sized suture thread (60). Furthermore, outer sheath (110) is formed of a seamless stainless steel tubing, such as a thin wall hypodermic stainless steel stock, in the present example. As will be apparent to those of ordinary skill in the art, outer sheath (110) and inner needle (130) may be formed of various suitable materials that will maintain durability when inserted into the cavity of a patient.

As seen in FIG. 6A, inner needle (130) includes a pair of notches (133). Notches (133) extend through inner needle (130) and comprise a catch undercut (134) and a release cam surface (135), respectively. Catch undercuts (134) have a hooked surface (136) and are configured to receive and hold suture thread (60) (see FIG. 4A) radially inwardly toward inner needle (130) when inner needle (130) is selectively maneuvered to catch suture thread (60) (see FIG. 4A). Release cam surfaces (135) are positioned between catch undercuts (134) and an outer radial surface (137) of inner needle (130). Release cam surfaces (135) extend proximally and radially outwardly from hooked surfaces (136) of catch undercuts (134) until becoming flush with outer radial surface (137) of inner needle (130). Release cam surfaces (135) are configured to urge suture thread (60) (see FIG. 4A) radially outwardly from catch undercuts (134) to thereby remove suture thread (60) (see FIG. 4A) from notches (133) when inner needle (130) is selectively maneuvered to release suture thread (60) (see FIG. 4A). Although not shown, it should be understood that inner needle (130) may comprise more or fewer notches (133) along inner needle (130) than that depicted in the present example.

Notches (133) are positioned along inner needle (130) at varying angular positions about longitudinal axis (131) such that notches (133) are oppositely positioned along inner needle (130). Notwithstanding the relative positioning of notches (133) relative to each other along inner needle (130), catch undercuts (134) are distally oriented on inner needle (130) relative to release cam surfaces (135). Although not shown, it should be understood that notches (133) may be positioned along inner needle (130) in an opposite orientation than that depicted in FIG. 6A. In this instance, catch undercuts (134) are proximally oriented on inner needle (130) relative to release cam surfaces (135). FIG. 6A shows suture passer (100) in the retracted position and needle head (132) contained within distal tip (116). With suture passer (100) in the retracted position, notches (133) remain covered within outer sheath (110) such that inserting suture passer (100) against tissue (17) will inhibit injury to the patient from the potential encounter of notches (133) against tissue (17) or any other portion of the patient's body.

Figure 6B:
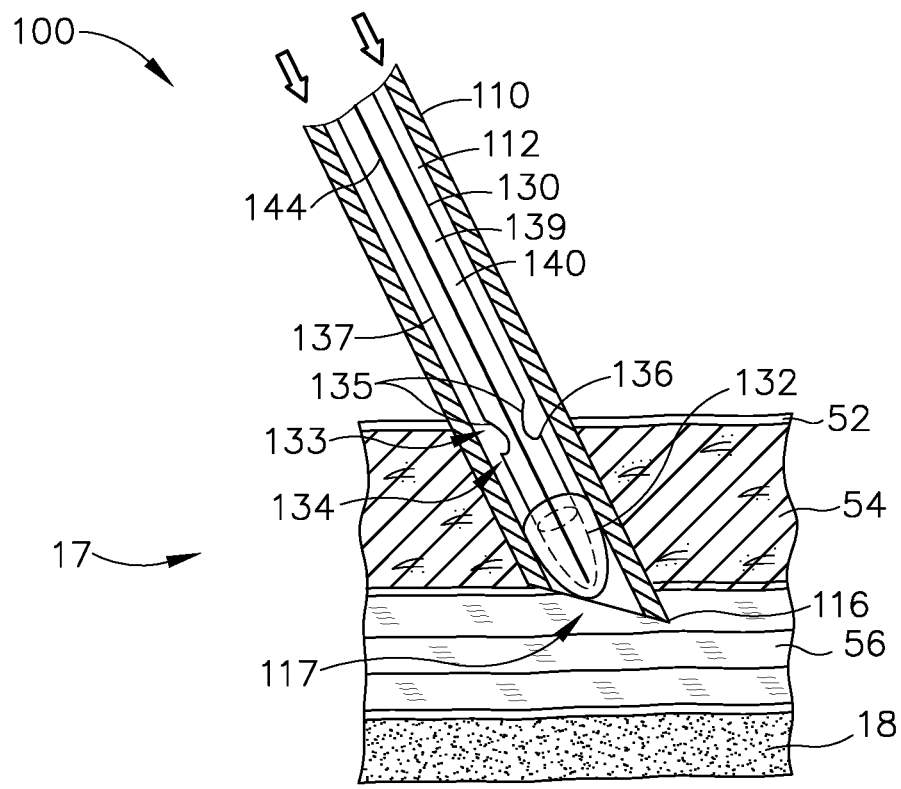
FIG. 6B depicts the partial sectional view of the suture passer similar to FIG. 6A, but with the suture passer inserted through the patient's outer layer of skin.
Figure 6C:
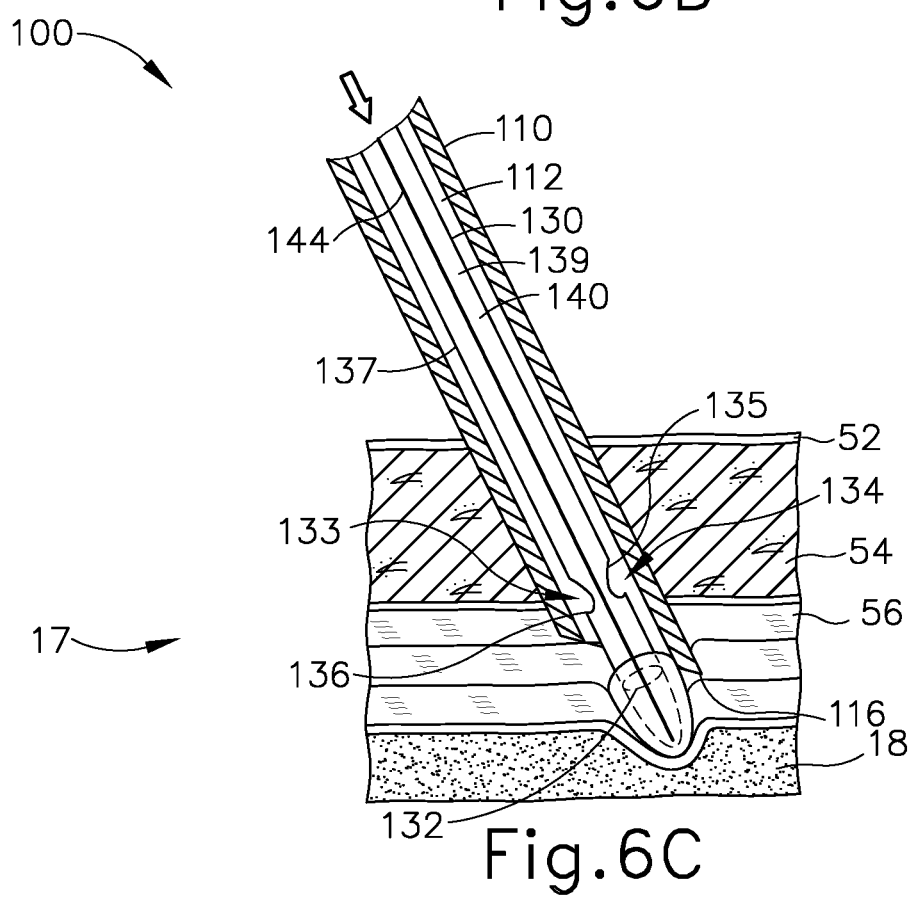
FIG. 6C depicts the partial sectional view of the suture passer similar to FIG. 6B, but with the inner needle in an extended position and a needle head of the inner needle in a contracted state.

In the present example, the clinician grasps housing (114) (see FIG. 5) to selectively position distal tip 116 against outer layer of skin (52). The exertion of force by the clinician on housing (114) results in distal tip (116) puncturing outer layer of skin (52) and inner layer of fat (54), as seen in FIG. 6B. Once positioned adjacent to tissue (17), the clinician exerts sufficient force upon driver (142) (see FIG. 5) to overcome the resilient bias created by the biasing member (not shown) to slidably translate inner needle (130) within outer lumen (112) in the distal direction, as seen in FIG. 6C. The biasing member (not shown) is forced into a compressed state while suture passer (100) is in the extended position and driver (142) is distally held towards housing (114) (see FIG. 5). As a merely illustrative example, the biasing member (not shown) may provide a spring rate ranging between approximately 2.3 lbs./inch to approximately 2.8 lbs./inch. Alternatively, the biasing member may include other various suitable spring rates that will allow for the translation of inner needle (130) within outer sheath (110) upon exertion of sufficient force. With suture passer (100) now being in the extended position, needle head (132) of inner needle (130) is distally extended through distal opening (117). As shown in FIG. 6C, this causes the tissue layers of fascia (56) to protrude or "tent" to some degree in cavity (18).

Figure 6D:
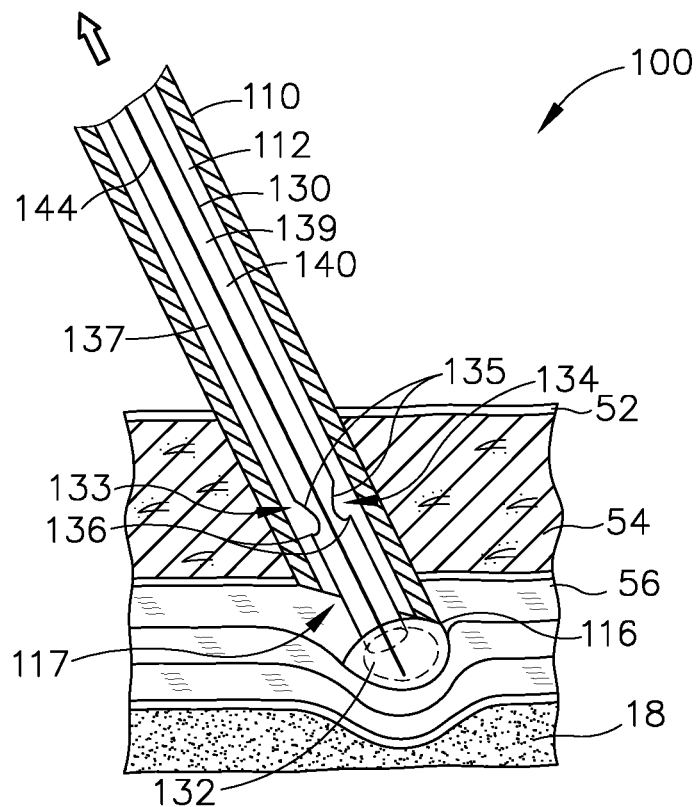
FIG. 6D depicts the partial sectional view of the suture passer similar to FIG. 6C, but with the needle head in an expanded state and the tissue tented outwards to thereby atraumatically indicate an anticipated puncture site.

FIG. 6D shows needle head (132) of inner needle (130) exposed beyond outer lumen (112) of outer sheath (110) at distal opening (117) when suture passer (100) is in the extended position, with head (132) expanded to the expanded state. In this instance, needle head (132) assumes a widened geometric shape configured to produce a low force impact against tissue (17) to emphasize a tenting effect on tissue (17). Needle head (132) is configured to transition to this enlarged geometric shape when cable (144) is moved proximally within inner lumen (139) to thereby pull needle head (132) in the proximal direction as discussed above in greater detail. The tenting effect created on tissue (17) provides the clinician with greater visibility, particularly when viewed through an endoscopic camera that is positioned within cavity (18) at an orientation viewing generally upwardly toward the insertion site of outer sheath (110) and inner needle (130). In this instance, the clinician is then able to determine whether the current location of suture passer (100), as indicated by the tenting of tissue (17) into cavity (18), is the desirable position for puncturing tissue (17).

In other words, by observing the location of the tenting effect on the layers of fascia (56) as shown in FIG. 6D, before outer sheath (110) and inner needle (130) pierce and penetrate the layers of fascia (56), the clinician may verify that the tenting effect is located at a desired position for outer sheath (110) and inner needle (130) to enter cavity (18) via the layers of fascia (56). If the clinician is not satisfied with the location of the observed tenting effect on the layers of fascia (56) as shown in FIG. 6D, the clinician may fully remove suture passer (100) from tissue (17) and then re-insert suture passer (100) at a different location and/or orientation. Thus, the clinician may repeat and reverse the steps shown in FIGS. 6A-6D, repositioning and/or reorienting suture passer (100) between each iteration of these steps, until the clinician is satisfied with the location of the observed tenting effect on the layers of fascia (56) as shown in FIG. 6D.

Figure 6E:
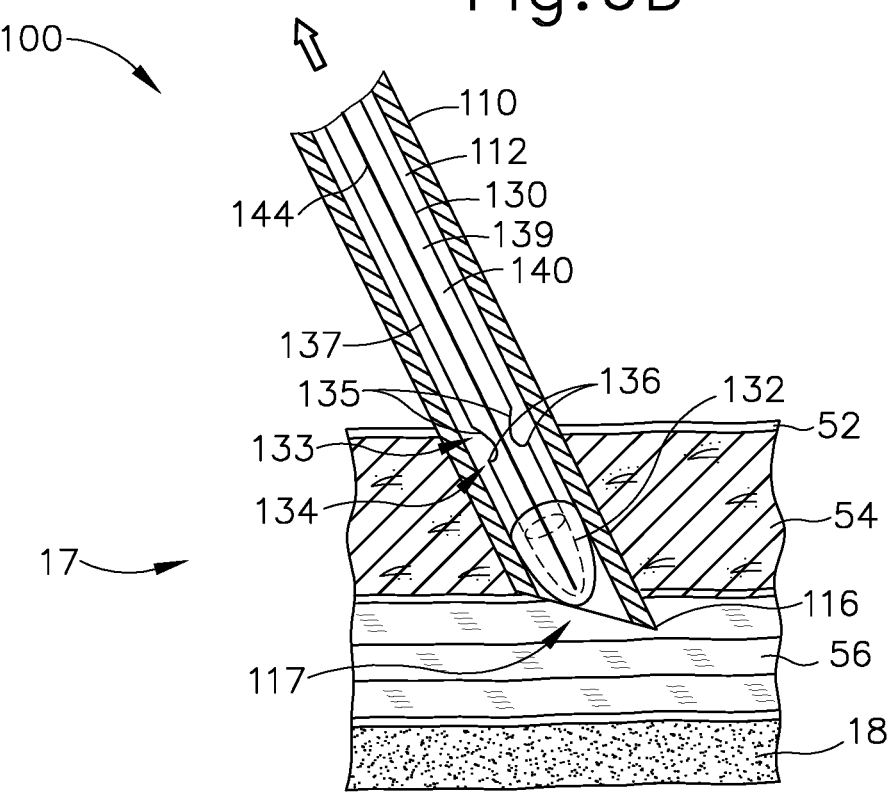
FIG. 6E depicts the partial sectional view of the suture passer similar to FIG. 6D, but with the needle head and the inner needle respectively returned to the contracted state and the retracted position.
Figure 6F:
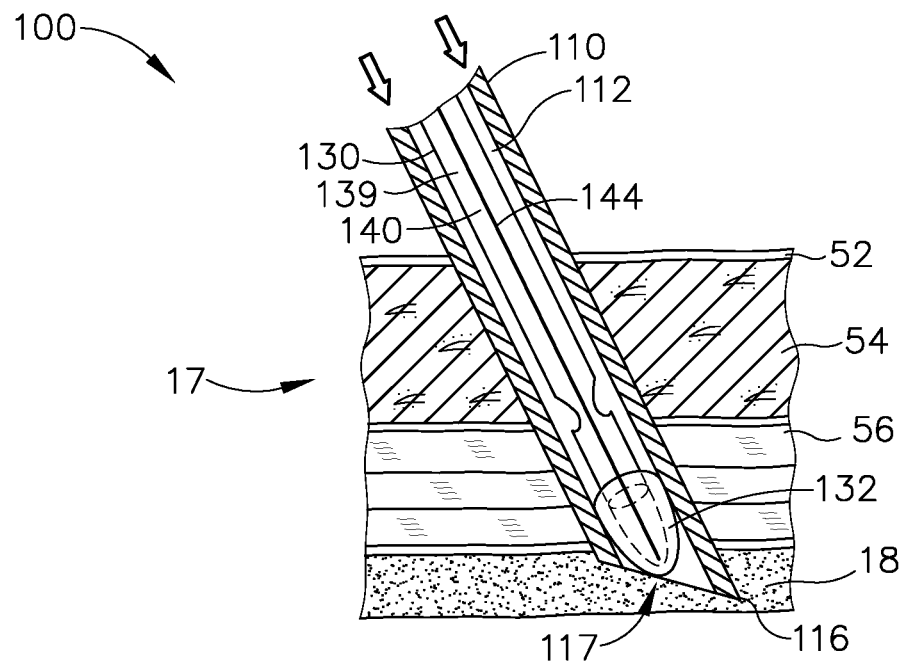
FIG. 6F depicts the partial sectional view of the suture passer similar to FIG. 6E, but with the outer needle puncturing through the tissue.
Figure 6G:
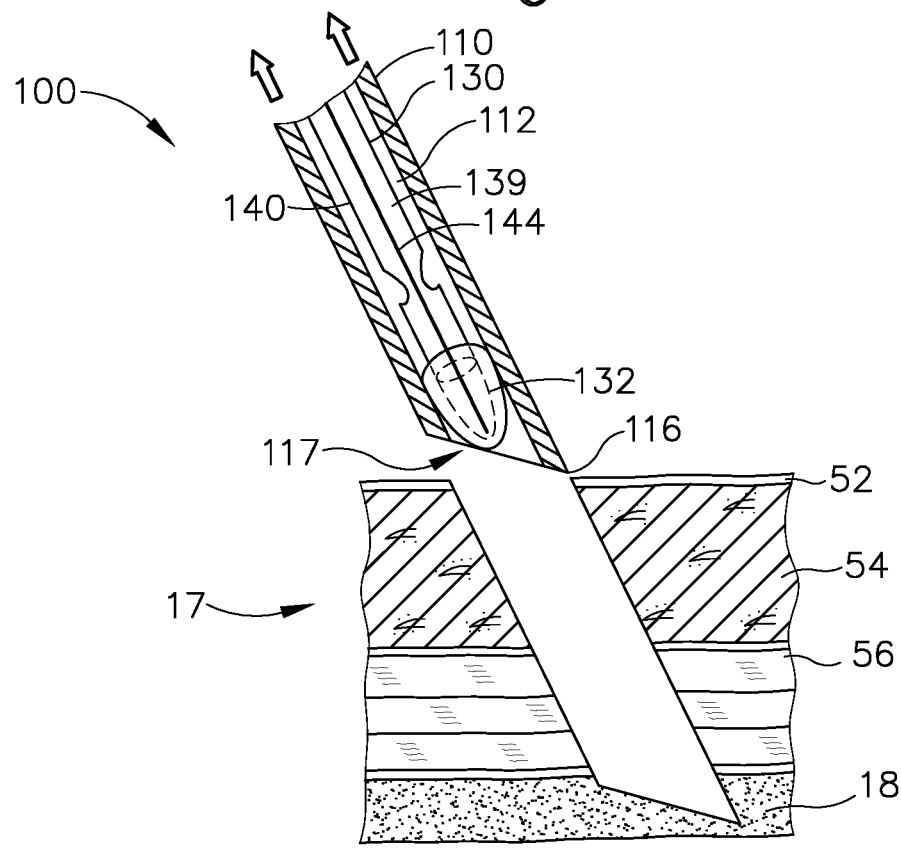
FIG. 6G depicts the partial cross-sectional view of the suture passer similar to FIG. 6F, but with the outer needle retracted from outer layer of skin thereby creating a tissue opening.

Once the clinician has confirmed that the current location of suture passer (100) is the desirable site for puncturing the layers of fascia (56), cable (144) is released to move distally through inner lumen (139) to thereby allow needle head (132) to return to the contracted state. Needle head (132) and inner needle (130) are then retracted into outer lumen (112) through distal opening (117) as seen in FIG. 6E. In addition, tissue (17) also reassumes its original characteristics and no longer extends into cavity (18) once needle head (132) and inner needle (130) are retracted into outer lumen (112). As shown in FIG. 6F, suture passer (100) is further advanced into the patient's body to puncture tissue (17) with distal tip (116) since needle head (132) and inner needle (130) are contained within outer sheath (110). Since suture passer (100) is capable of performing both functions of identifying the penetration site and subsequently puncturing tissue (17), it is more likely that clinician will puncture tissue (17) at the desired location.

After reaching the state shown in FIG. 6F, inner needle (130) may be advanced distally and then retracted proximally to capture a suture thread (60) within a notch (133). For instance, an additional exertion of force on driver (142) extends notches (133) beyond outer lumen (112) of outer sheath (110). In this instance, inner needle (130) and notches (133) are configured to be physically maneuvered within the patient's body to catch and subsequently release suture thread (60) (see FIG. 4A). After suture passer (100) captures suture thread (60) within cavity (18), suture passer (100) may then be retracted proximally from tissue (17) to pull the captured suture thread (60) through tissue (17). Suture passer (100) may then release suture thread (60) for subsequent manipulation of suture thread (60). After suture passer (100) has been retracted from and reinserted through tissue (17) to reach cavity (18) a desired number of times, suture passer (100) may be finally removed from tissue (17) as shown in FIG. 6G. In some instances, this may leave a passageway through tissue (17) that needs to be closed using a suture, staple, adhesive, and/or any other suitable devices or techniques. In some other instances, the passageway left in tissue (17) may be small enough to be self-sealing, such that a suture, staple, adhesive, and/or any other device or technique is not needed in order to close the passageway left by suture passer (100) in tissue (17).

ii. Exemplary Outer Needle with Circular Sharpened Edge Tip

Figure 7:
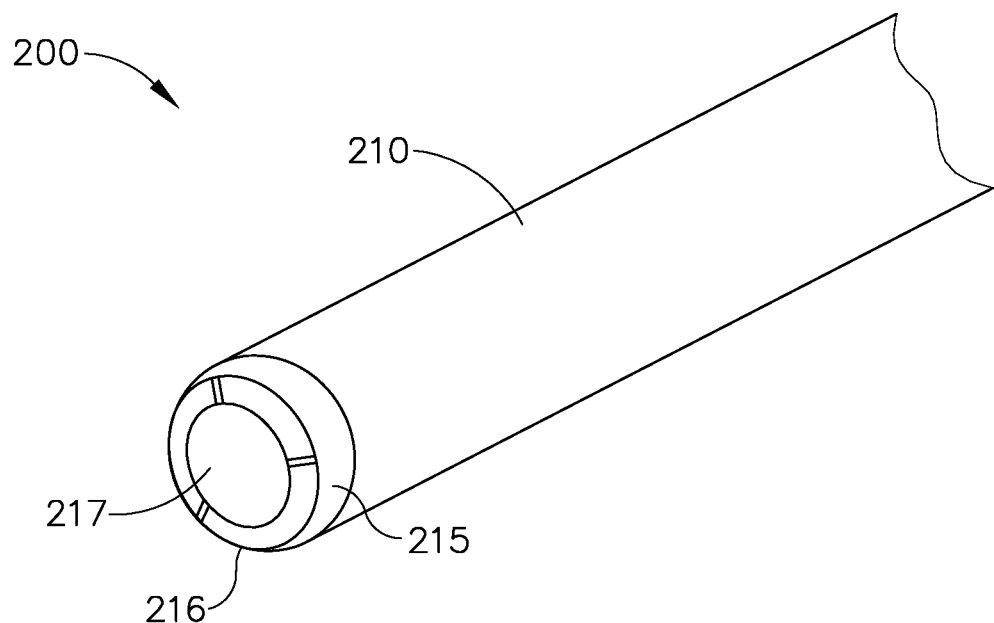
FIG. 7 depicts an enlarged perspective view of a second exemplary suture passer with an inner needle slidably received within an outer needle having a circular sharpened edge.
Figure 8:
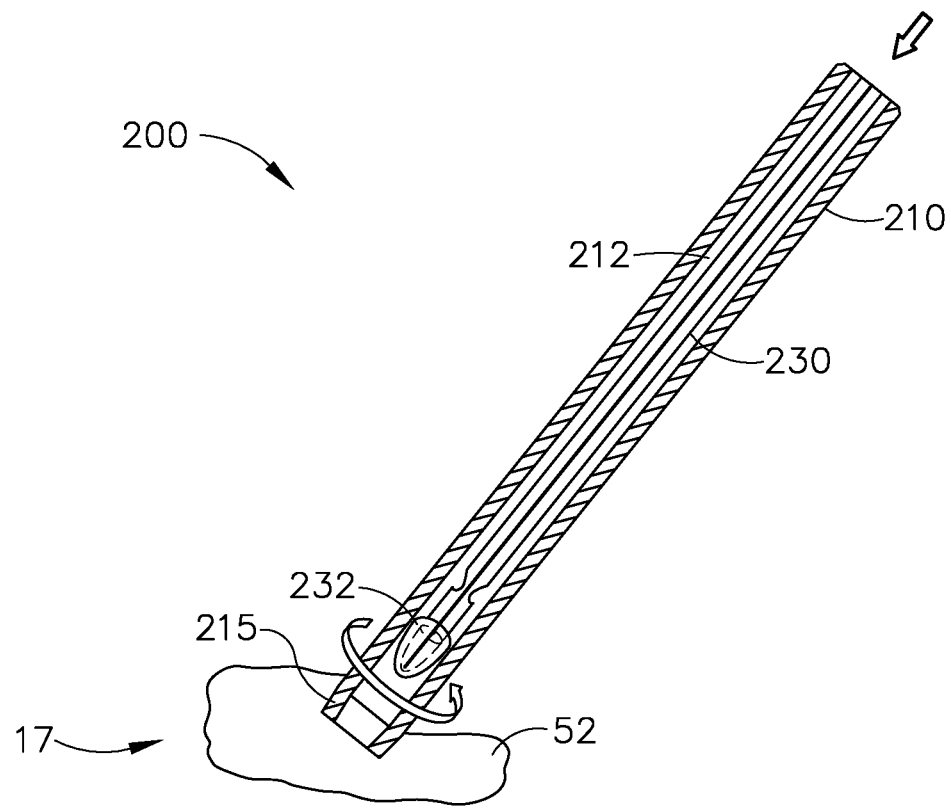
FIG. 8 depicts a partial cross-sectional view of the suture passer of FIG. 7, taken generally along a centerline thereof, with the suture passer driven into the outer layer of skin and the inner needle in a retracted position contained within the outer needle.

FIGS. 7-8 illustrate a second exemplary suture passer (200) comprising an outer sheath (210) and inner needle (230) contained therein. Except as otherwise described below, outer sheath (210) is operable similar to outer sheath (110) (see FIG. 5) described above. Outer sheath (210)

includes a distal tip (216) that has a distal end with a circular sharpened edge tip (215) about a longitudinal axis (not shown). Sharpened edge tip (215) is configured to puncture tissue (17) when outer sheath (210) is rotated and driven distally against tissue (17). Distal tip (216) further includes a distal opening (217) coaxially positioned inward of sharpened edge tip (215) such that sharpened edge tip (215) surrounds distal opening (217). Inner needle (230) is slidably contained within an outer lumen (212) of outer sheath (210) for use against tissue (17) as discussed above. Suture passer (200) of this example is thus operable in the same way as suture passer (100) described above. The difference between suture passers (100, 200) lies in the fact that distal tip (116) of outer sheath (110) is obliquely oriented along the longitudinal axis of outer sheath (110); while distal tip (216) of outer sheath (210) is perpendicular to the longitudinal axis of outer sheath (210).

B. Exemplary Suture Passer with a Resiliently Pointed Tip

Figure 9:
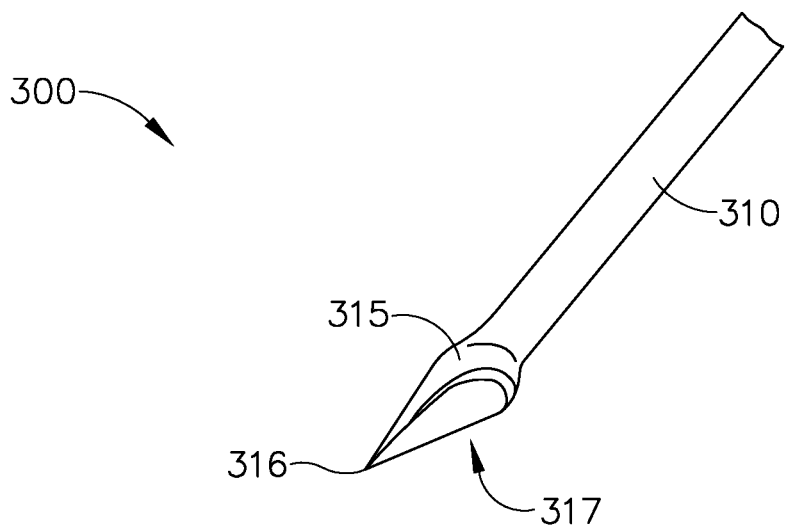
FIG. 9 depicts an enlarged perspective view of a third exemplary alternative suture passer with a pointed tip and a bulbous shape.
Figure 10A:
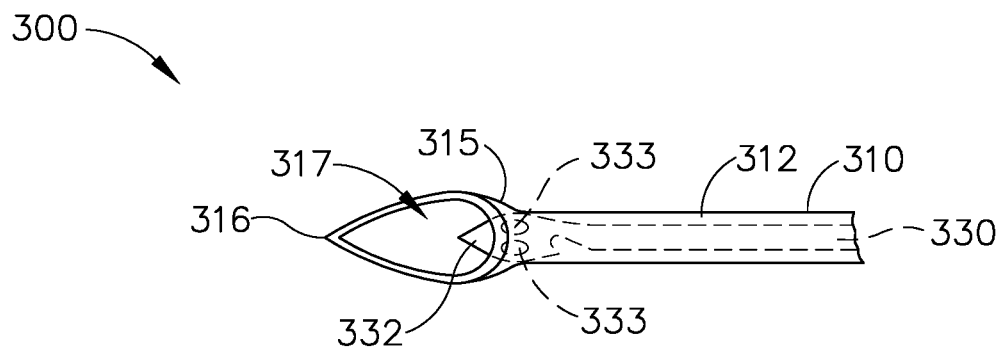
FIG. 10A depicts an enlarged top view of the suture passer of FIG. 9, with an inner needle in a retracted position contained within an outer needle and a head of the inner needle in a contracted state.
Figure 10B:
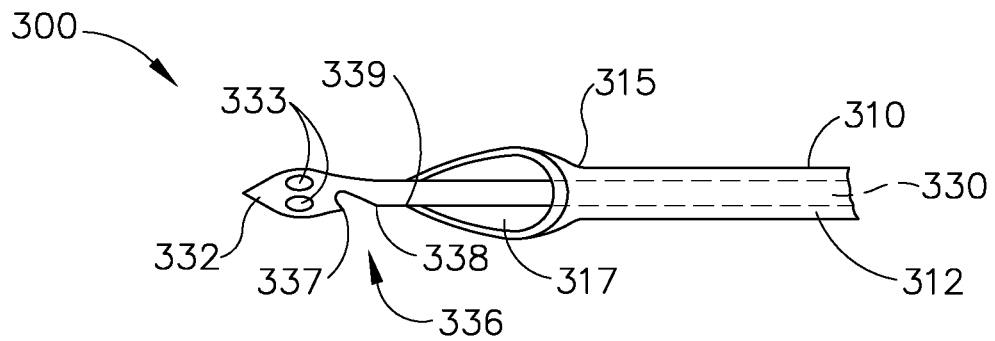
FIG. 10B depicts the enlarged top view of the suture passer similar to FIG. 10A, but with the inner needle in an extended position and the needle head in an expanded state.

FIGS. 9-10B depict a third exemplary suture passer (300) comprising an outer sheath (310) and an inner needle (330) contained therein. Except as otherwise described below, outer sheath (310) and inner needle (330) are respectively similar to outer sheath (110) (see FIG. 5) and inner needle (130) (see FIG. 5) described above. A distal portion of outer sheath (310) includes a distal tip (316), a bulbous neck (315), and a distal opening (317). Distal tip (316) has a pointed end positioned distally along outer sheath (310) relative to bulbous neck (315) and distal opening (317). Distal tip (316) is also configured to puncture tissue (17) (see FIG. 6A) when outer sheath (310) is driven against tissue (17) (see FIG. 6A).

As seen in FIG. 10A, inner needle (330) includes a distal end having a head (332) that is resiliently biased to an expanded state. However, with head (332) positioned in outer lumen (312), head (332) is laterally constrained to a contracted state within outer sheath (310). Head (332) includes a pair of flex apertures (333) that are configured to facilitate the resilient contraction of head (332) when in the contracted state. Any other suitable number of flex apertures (333) may be provided. Bulbous neck (315) has a wider diameter than outer lumen (312) along the longitudinal length of outer sheath (310) such that bulbous neck (315) allows head (332), including flex apertures (333), to resiliently expand from the contracted state to the expanded state as inner needle (330) distally translates from a retracted position shown in FIG. 10A toward an extended position shown in FIG. 10B.

In the present example, flex apertures (333) are configured to provide for compressible deformation of head (332) to thereby reduce the frictional resistance between head (332) and outer lumen (312) during translation of inner needle (330) between extended and retracted positions. Upon inner needle (330) distally translating to the extended position, where head (332) extends beyond distal opening (317), flex apertures (333) become enlarged and thereby cause head (332) to transition to the expanded state, as seen in FIG. 10B.

In the present example, head (332) further includes a notch (336) that is configured to receive and hold suture thread (60) (see FIG. 4A) radially inwardly toward inner needle (330) when inner needle (330) is selectively maneuvered to catch suture thread (60). Notch (336) may be further configured to urge suture thread (60) (see FIG. 4A) radially outwardly to thereby release suture thread (60) (see FIG. 4A) from notch (336) when inner needle (130) is selectively maneuvered to release suture thread (see FIG. 4A). Similar to notches (133) (see FIG. 6A), notch (336) includes a catch undercut (337) and a release cam surface (338) positioned between catch undercut (337) and an outer radial surface (339) of inner needle (330).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an outer sheath defining a lumen; and (b) an inner needle slidably disposed in the outer sheath, wherein the inner needle comprises: (i) a shaft, (ii) a driver configured to drive the shaft relative to the outer sheath from a first position to a second position, (iii) at least one suture capturing feature, wherein the at least one suture capturing feature is configured to cooperate with the outer sheath to thereby selectively capture and release a suture based on positioning of the shaft relative to the outer sheath, and (iv) a head secured to the shaft at an end opposite the driver, wherein the head is configured to transition between a contracted state and an expanded state.

Example 2

The surgical instrument of Example 1, wherein the at least one suture capturing feature comprises at least one notch formed in the head.

Example 3

The surgical instrument of any one or more of Examples 1 through 2, wherein the outer sheath comprises an outer needle having a distal tip.

Example 4

The surgical instrument of Example 3, wherein the distal tip of the outer needle has a pointed end such that the distal tip is configured to penetrate tissue.

Example 5

The surgical instrument of any one or more of Examples 3 through 4, wherein the distal tip of the outer needle has a sharpened edge such that the distal tip is configured to penetrate tissue.

Example 6

The surgical instrument of any one or more of Examples 3 through 5, wherein the head is configured to be confined within the tip when the inner needle is in the first position, wherein the head is configured to extend beyond the tip when the inner needle is translated to the second position by the driver.

Example 7

The surgical instrument of Example 6, wherein the shaft defines an inner lumen along a longitudinal axis, wherein the inner needle further comprises a cable slidably disposed within the inner lumen and operatively connected to an actuator.

Example 8

The surgical instrument of Example 7, wherein the cable is operatively connected to the head at an end opposite the actuator, wherein the cable is operable to radially expand the head from the contracted state to the expanded state when the inner needle is in the second position.

Example 9

The surgical instrument of Example 8, wherein the head has a blunt end such that the head is atraumatic.

Example 10

The surgical instrument of any one or more of Examples 8 through 9, wherein the head has a sharp end such that the head is configured to pierce tissue.

Example 11

The surgical instrument of Example 10, wherein the head is resiliently biased to the expanded state such that the head is configured to resiliently expand from the contracted state to the expanded state when the inner needle is translated from the first position to the second position.

Example 12

The surgical instrument of Example 11, wherein the outer needle defines an outer lumen having a first diameter, wherein the outer needle includes a bulbous shape having a second diameter, wherein the first diameter is smaller than the second diameter and the bulbous shape is proximal to the distal tip such that the head is configured to resiliently expand in the second diameter of the bulbous shape upon translation from the first position to the second position.

Example 13

The surgical instrument of any one or more of Examples 11 through 12, wherein the head includes at least one flex aperture, wherein the at least one flex aperture is configured to facilitate the resilient contraction of the head when in the contracted state.

Example 14

The surgical instrument of Example 13, wherein the at least one flex aperture is configured to reduce frictional resistance between the head and the outer needle upon translation of the inner needle relative to the outer needle.

Example 15

The surgical instrument of Example 14, wherein the at least one flex aperture is configured to be enlarged when the head is in the expanded state in the second position.

Example 16

A surgical instrument comprising: (a) a needle including at least one notch, wherein the notch is configured to capture a suture thread; and (b) a needle head fixedly attached to the needle, wherein the needle head is formed of a resilient material such that the needle head is operable to resiliently expand relative to a central axis from a contracted state to an expanded state.

Example 17

The surgical instrument of Example 16, further comprising a shaft including an opening at a distal end portion, wherein the needle is configured to be movably contained within the shaft when in a first position, wherein the needle is configured to protrude beyond the shaft through the opening when in a second position.

Example 18

The surgical instrument of Example 17, further comprising a cable movably contained within the needle, wherein the cable is operable to resiliently expand the needle head from the contracted state to the expanded state.

Example 19

The surgical instrument of any one or more of Examples 17 through 18, wherein the needle head includes one or more apertures configured to deform when the head is in the contracted state, wherein the one or more apertures is operable to reduce frictional resistance between the head and the shaft when the needle is in the first position.

Example 20

A method of indicating a tissue penetration site with an apparatus including a needle having a head configured to change profiles from a contracted state to an expanded state, the method comprising: (a) advancing the head proximate to the tissue penetration site; (b) forcing the head against a surface of the tissue; and (c) expanding the head from a contracted state to an expanded state to deform the tissue without penetrating the tissue, thereby indicate the tissue penetration site.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

The teachings presented herein may be further combined with various teachings of any one or more of the following: U.S. App. No. 15/637,690, entitled "Needle Guide Instrument with Traverse Suture Capture Feature," filed on Jun. 29, 2017, published as U.S. Pub. No. 2019/0000443 on Jan. 3, 2019, the disclosure of which is incorporated by reference herein; U.S. App. No. 15/637,702, issued as U.S. Pat. No. 10,639,029 on May 5, 2020, entitled "Suture Grasping Instrument," filed on Jun. 29, 2017, the disclosure of which is incorporated by reference herein; U.S. App. No. 15/638,683, issued as U.S. Pat. No. 10,639,068 on May 5, 2020, incorporated by reference above; U.S. App. No. 15/637,688, incorporated by reference above, issued as U.S. Pat. No. 10,485,580 on Nov. 26, 2019; U.S. App. No. 15/637,696, entitled "Trocar Obturator with Transverse Needle Ports," filed on Jun. 29, 2017, the disclosure of which is incorporated by reference herein, published as U.S. Pub. No. 2019/0000506 on Jan. 3, 2019; U.S. App. No. 15/637,707, entitled "Surgical Port with Wound Closure Channels," filed on Jun. 29, 2017, the disclosure of which is incorporated by reference herein, issued as U.S. Pat. No. 10,568,619 on Feb. 25, 2020; U.S. App. No. 15/637,735, entitled "Trocar Obturator with Detachable Rotary Tissue Fastener," filed on Jun. 29, 2017, the disclosure of which is incorporated by reference herein, published as U.S. Pub. No. 2019/0000502 on Jan. 3, 2019; U.S. App. No. 15/637,778, entitled "Method of Suturing a Trocar Patch Incision," filed on Jun. 29, 2017, the disclosure of which is incorporated by reference herein, published as U.S. Pub. No. 2019/000496 on Jan. 3, 2019; and/or other patents and patent application publications incorporated by reference above.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an outer sheath defining a lumen; and
   (b) an inner needle slidably disposed in the outer sheath, wherein the inner needle comprises:
      (i) a shaft that includes a distal end,
      (ii) a driver configured to drive the shaft relative to the outer sheath from a first position to a second position,
      (iii) at least one suture capturing feature, wherein the at least one suture capturing feature is configured to cooperate with the outer sheath to thereby selectively capture and release a suture based on positioning of the shaft relative to the outer sheath, and
      (iv) a head secured to the shaft at an end opposite the driver, wherein the head includes an atraumatic distal end, wherein the head is deformable and configured to transition between a contracted state and an expanded state, wherein proximal actuation of the driver is configured to pull the atraumatic distal end of the head proximally toward the distal end of the shaft to transition the head to the expanded state.

2. The surgical instrument of claim 1, wherein the at least one suture capturing feature comprises at least one notch formed in the head.

3. The surgical instrument of claim 1, wherein the outer sheath comprises an outer needle having a distal tip.

4. The surgical instrument of claim 3, wherein the distal tip of the outer needle has a pointed end such that the distal tip is configured to penetrate tissue.

5. The surgical instrument of claim 3, wherein the distal tip of the outer needle has a sharpened edge such that the distal tip is configured to penetrate tissue.

6. The surgical instrument of claim 3, wherein the head is configured to be confined within the distal tip when the inner needle is in the first position, wherein the head is configured to extend beyond the distal tip when the inner needle is translated to the second position by the driver.

7. The surgical instrument of claim 6, wherein the shaft defines an inner lumen along a longitudinal axis, wherein the inner needle further comprises a cable slidably disposed within the inner lumen and operatively connected to an actuator.

8. The surgical instrument of claim 7, wherein the cable is operatively connected to the head at an end opposite the actuator, wherein the cable is operable to radially expand the head from the contracted state to the expanded state when the inner needle is in the second position.

9. The surgical instrument of claim 8, wherein the atraumatic distal end is a blunt distal end such that the head is atraumatic.

10. The surgical instrument of claim 1, wherein the head is resiliently biased to the expanded state such that the head is configured to resiliently expand from the contracted state to the expanded state when the inner needle is translated from the first position to the second position.

11. The surgical instrument of claim 10, wherein the outer sheath comprises an outer needle having a distal tip, wherein the outer needle defines an outer lumen having a first diameter, wherein the outer needle includes a bulbous shape having a second diameter, wherein the first diameter is smaller than the second diameter and the bulbous shape is proximal to the distal tip such that the head is configured to resiliently expand in the second diameter of the bulbous shape upon translation from the first position to the second position.

12. The surgical instrument of claim 1, wherein the head of the inner needle is formed from a different material than the shaft of the inner needle.

13. The surgical instrument of claim 1, wherein the atraumatic distal end is formed from a deflectable material.

14. The surgical instrument of claim 13, wherein the deflectable material is an elastomer.

15. The surgical instrument of claim 1, wherein the head is configured to umbrella radially outwardly to the expanded state relative to a longitudinal axis of the inner needle when the driver is in the second position.

16. The surgical instrument of claim 1, wherein proximal actuation of the driver is configured to pull the atraumatic distal end of the head proximally toward the distal end of the shaft while a proximal portion of the head abuts against the distal end of the shaft to transition the head to the expanded state.

17. The surgical instrument of claim 1, wherein the lumen of the outer sheath defines a longitudinal axis, wherein the outer sheath includes a distal tip that is obliquely oriented along the longitudinal axis of the outer sheath.

18. The surgical instrument of claim 1, wherein the lumen of the outer sheath defines a longitudinal axis, wherein the outer sheath includes a distal tip that is perpendicular to the longitudinal axis of the outer sheath.

19. A surgical instrument comprising:
   (a) a needle including at least one notch, wherein the notch is configured to capture a suture thread;
   (b) a blunt needle head irremovably attached to the needle, wherein the needle head is formed of a resilient material such that the needle head is operable to resiliently expand relative to a central axis from a contracted state to an expanded state;
   (c) a cable movably contained within the needle, wherein the cable is operable to resiliently expand the needle head from the contracted state to the expanded state; and
   (d) a shaft including an opening at a distal end portion and a sharp distal tip, wherein the blunt needle head is configured to be movably contained within the shaft when the blunt needle head is in a first position, wherein the blunt needle head is configured to protrude beyond the shaft through the opening when the blunt needle head is in a second position.

20. A surgical instrument comprising:
(a) an outer sheath defining a lumen; and
(b) an inner needle slidably disposed in the outer sheath, wherein the inner needle comprises:
 (i) a shaft,
 (ii) a driver configured to drive the shaft relative to the outer sheath from a first position to a second position,
 (iii) at least one suture capturing feature, wherein the at least one suture capturing feature is configured to cooperate with the outer sheath to thereby selectively capture and release a suture based on positioning of the shaft relative to the outer sheath, and
 (iv) a head secured to the shaft at an end opposite the driver, wherein the head includes at least one flex aperture configured to facilitate a resilient transition between a contracted state and an expanded state, wherein the at least one flex aperture is completely enclosed within an outer periphery of the head in both the contracted state and the expanded state, wherein the at least one flex aperture is disposed distal to the at least one suture capturing feature.

* * * * *